United States Patent [19]

Rieker et al.

[11] Patent Number: 4,816,588

[45] Date of Patent: Mar. 28, 1989

[54] METHOD FOR THE PREPARATION OF PYRIDINE-2,3-DICARBOXYLIC ACIDS

[75] Inventors: William F. Rieker, Plainsboro; William A. Daniels, Belle Mead, both of N.J.

[73] Assignee: American Cyanamid Company, Stamford, Conn.

[21] Appl. No.: 85,916

[22] Filed: Aug. 19, 1987

Related U.S. Application Data

[63] Continuation-in-part of Ser. No. 906,713, Sep. 12, 1986, abandoned.

[51] Int. Cl.$^4$ .................. C07D 213/80; C07D 213/89; C07D 491/048; C07D 445/04
[52] U.S. Cl. ..................................... 546/321; 546/113; 546/114; 546/115; 546/116; 546/320
[58] Field of Search ............... 546/320, 113, 114, 115, 546/116, 321

[56] References Cited

U.S. PATENT DOCUMENTS

| 3,027,380 | 3/1962 | Leonard . | |
|---|---|---|---|
| 3,741,976 | 6/1973 | Stocker | 546/320 |
| 3,748,336 | 7/1973 | Stocker | 546/320 |
| 3,829,432 | 8/1974 | Hanotier . | |
| 4,439,607 | 5/1984 | Drabb | 546/89 |
| 4,518,780 | 5/1985 | Barton | 546/167 |
| 4,537,971 | 8/1985 | Rebhahn et al. | 546/320 |
| 4,623,726 | 11/1986 | Daniels | 546/320 |

FOREIGN PATENT DOCUMENTS

| 0041623 | 6/1985 | European Pat. Off. . |
| 3150005 | 6/1983 | Fed. Rep. of Germany . |
| 3345223 | 6/1985 | Fed. Rep. of Germany . |
| 880592 | 10/1961 | United Kingdom . |

OTHER PUBLICATIONS

Chemical Abstracts 82: 170704t (of French 2193820).
C. Riedel, Chem. Ber. 16, 1609–1616 (1883).
O. Doebner et al. Chem. Ber. 18, 1640–1646.
V. Oakes et al., *J. Chem. Soc.*, 4433 (1956).
B. Blank et al., J. Med. Chem, Vol. 17, No. 10 1065 (1974).

*Primary Examiner*—Robert W. Ramsuer
*Attorney, Agent, or Firm*—Alice C. Brennan

[57] ABSTRACT

The present invention provides a novel method for the preparation of pyridine-2,3-dicarboxylic acids by the oxidation of 8-substituted quinolines.

11 Claims, No Drawings

METHOD FOR THE PREPARATION OF PYRIDINE-2,3-DICARBOXYLIC ACIDS

BACKGROUND OF THE INVENTION

This application is a continuation-in-part of application Ser. No. 906,713, filed Sept. 12, 1986, abandoned.

Novel pyridine and quinoline imidazolinone compounds including 5-substituted, 6-substituted and 5,6-disubstituted-2-(4-isopropyl-4-methyl-5-oxo-2-imidazolin-2-yl)nicotinic acid, esters and salts thereof are disclosed in European Patent Application No. 0 041 623 (1985). Herbicidal imidazolinyl nicotinic acids may readily be prepared by the procedure described in U.S. Pat. No. 4,518,780 (1985) by cyclization under basic conditions of an appropriately substituted 2-carbamoyl-nicotinic acid which, in turn may be prepared by the reaction of a substituted 2,3-pyridine dicarboxylic acid anhydride and appropriately substituted aminocarboxamide or aminothiocarboxamide.

Preparation of starting 2,3-pyridine-dicarboxylic acid anhydrides from the appropriate 2,3-pyridinedicarboxylic acid may be accomplished by many procedures well known in the art, including the method described in U.S. Pat. No. 4,439,607.

Unfortunately, literature methods for preparing pyridine-2,3-dicarboxylic acids are limited. Methods requiring the use of transition metal catalysts in oxidizing quinolines such as those described in German Patents DE. No. 3,345,223; DE No. 3,150,005; French Patent FR No. 2,193,820; and U.S. Pat. No. 3,829,432 are limited to the preparation of either the unsubstituted pyridine 2,3-dicarboxylic acid or to the preparation of those compounds which do not contain substituents which are also oxidized during the process.

Early reports describing the preparation of alkyl substituted pyridine-2,3-dicarboxylic acids by oxidative methods stemmed from interest in lepidine (4-methylquinoline).

S. Hoogeweff and W. A. van Dorp Chem. Ber. 13, 1639 reported that 4-methylpyridine-2,3-dicarboxylic acid could be isolated from the stepwise oxidation of lepidine with permanganate.

C. Riedel, Chem. Ber. 16 1609–1616 citing the above work of Hoogeweff and van Dorp, proposed in a like manner to conduct a reaction sequence of oxidizing β-ethylbenzoquinoline to β-ethylpyridine-2,3-carboxylic acid, followed by decarboxylation by distillation over calcium hydroxide to obtain β-ethylpyridine which would, upon further oxidation yield β-pyridinecarboxylic acid, as a method to confirm the position of the carboxlyic acid substituent, as illustrated in the flow diagram below.

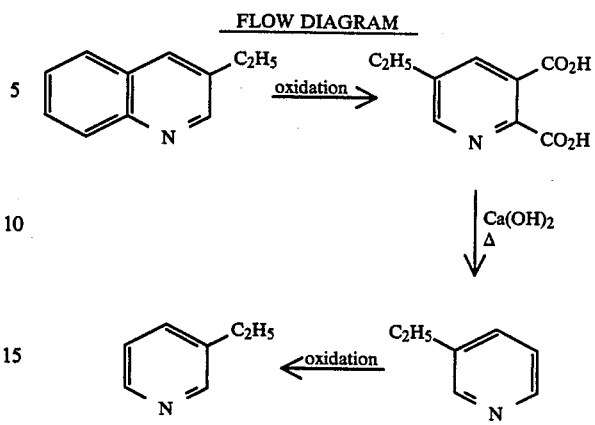

FLOW DIAGRAM

Riedel reported that oxidation of β-ethylbenzoquinoline with chromic acid yielded β-benzoquinolinecarboxylic acid and that further oxidation of this compound with potassiuim permanganate under basic conditions yielded the corresponding pyridinetricarboxylic acid. Based upon this result, Reidel drew the conclusion that the difference in behavior of β-ethylquinoline and lepidine was due to the difference in the length of the alkyl chain (ethyl vs methyl).

O. Doebner and W. van Miller Chem. Ber. 18, 1640–1646, commented on the conclusion drawn by Riedel, citing H. Weidel, Monatshefte F. Chem. 3 79 "who showed that, in the oxidation of cincholepidine with chromic acid instead of with potassium permanganate, it is not the benzene group but the methyl group that is attacked". Doebner and van Miller additionally demonstrated that the oxidation of β-methylquinoline with chromic acid also resulted in oxidation of the methyl group.

Further support for the Doebner and von Miller publication has been evidenced by the potassium permanganate oxidation of 3-ethylquinoline under basic conditions (the conditions employed by Reidel for the subsequent oxidation of β-benzoquinolinecarboxylic acid to the corresponding pyridinetricarboxylic acid) to produce 5-ethylpyridine-2,3-dicarboxylic acid in 6 to 7% yields.

More recent oxidative methods which have been reported to be suitable for the preparation of pyridine-2,3-dicarboxylic acids containing substituents in the 4, 5 and 6 position of the pyridine ring include:

1. the preparation of 5-methyl-pyridine-2,3-dicarboxylic acid by nitric acid oxidation of 8-hydroxy-3-methylquinoline which was obtained by Skraup reaction of o-aminophenol with α-methylacraldehyde; V. Oakes and H. N. Rydon, J. Chem. Soc., 4433 (1956); and 2. the preparation of 4-methyl-pyridine-2,3-dicarboxylic acid, in 65% yield; 5-methyl-pyridine-2,3-dicarboxylic acid, in 50% yield; and 6-methyl-pyridine-2,3-dicarboxylic acid in 57% yield by the oxidation of the corresponding 4, 5 or 6 methyl 8-hydroxyquinoline with nitric acid and the preparation of 5-chloro-pyridine-2,3-dicarboxylic acid in 31% yield by the oxidation of 3-chloroquinoline with KMnO₄; B. Blank et al., J. Med. Chem., Vol. 17, No. 10, 1065 (1974).

We have shown that oxidation of 3-ethyl-8-hydroxyquinoline (prepared in 39% yield by the Skraup reaction of o-aminophenol with 2-ethylacrolein), with nitric acid as described in the above publications yields: 5- ethyl-pyridine-2,3-dicarboxylic acid having mp 146°–147° C. in 40% yield.

3. GB No. 880,592 published Oct. 25, 1961 describes a method of preparing substituted and unsubstituted pyridine-2,3-dicarboxylic acids by ozonolysis of benzazines such as quinalidine, lepidine, carbostyril, 8-hydroxyquinoline and 2-aminoquinoline in the presence of a sufficient amount of a mineral acid such as nitric acid, sulfuric acid or phosphoric acid to form a salt of the benzazine.

We have shown that ozonolysis of 3-ethyl-quinoline and 3-ethyl-8-hydroxyquinoline using the procedure described above yields 5-ethyl-pyridine-2,3-dicarboxylic acid in 25% yield and 60% yield respectively.

An oxidative method for the preparation of pyridine-2,3-dicarboxylic acids is also disclosed in U.S. Pat. No. 3,027,380 issued Mar. 27, 1962 which describes the preparation of 5-fluoropyridine-2,3-dicarboxylic acid by the action of nascent or atomic oxygen on 3-fluoroquinoline.

While the above literature procedures utilizing permanganate, nitric acid and ozone have demonstrated applicability for the preparation of pyridine-2,3-dicarboxylic acids containing substituents in the pyridine ring such as methyl, ethyl, chloro and the like, they are not completely satisfactory for large scale commercial production.

It is an object of this invention to provide a novel method for the preparation of pyridine-2,3-dicarboxylic acids which may contain a variety of substituents on the pyridine ring including oxidizable groups such as alkyl groups, under basic conditions.

SUMMARY OF THE INVENTION

The invention relates to a method for the preparation of unsubstituted or substituted pyridine-2,3-dicarboxylic acids of formula I

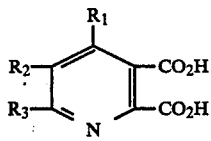

wherein $R_1$, $R_2$ and $R_3$ are each hydrogen, $C_1$–$C_6$ alkyl, hydroxy-$C_1$–$C_6$ alkyl, $C_1$–$C_6$ alkoxy, phenoxy, $C_1$–$C_4$ haloalkyl, nitro, hydroxy, amino, $C_1$–$C_4$ alkylamino, diloweralkylamino or $C_1C_4$ alkylamino, diloweralkylamino or $C_1$–$C_4$ alkylsulfonyl group, carboxy, acyl, amido; or phenyl optionally substituted with one $C_1$–$C_4$ alkyl, $C_1$–$C_4$ alkoxy or halogen; difluoromethoxy, trifluoromethoxy, 1,1,2,2-tetrafluoroethoxy, $C_3C_8$ straight or branched alkenyloxy optionally substituted with one to three halogens, or $C_3$–$C_8$ straight or branched alkynyloxy optionally substituted with one to three halogens;

and when taken together, $R_2$ and $R_3$ may form a ring which may optionally be substituted, in which $R_2R_3$ are represented by $(CH_2)_2$—Q— or —$(CH)_2$—Q—, wherein Q is oxygen, sulfur, or nitrogen, with the proviso that $R_1$ is hydrogen; comprising oxidizing a substituted quinoline of formula II

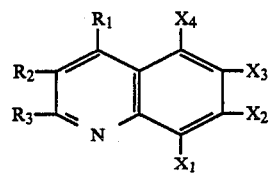

wherein $R_1$, $R_2$ and $R_3$ are as described for formula I above; $X_1$, $X_2$, $X_3$, and $X_4$ are each hydrogen, hydroxy, $SO_3H$, $SO_2Cl$, SH, Cl, F, Br, I, $CO_2H$, $NO_2$, $NH_2$, or $NHR$, $NR_2$, $CONR_2$ or COR wherein R is $C_1$–$C_4$ alkyl; with the proviso that one of $X_1$, $X_2$, $X_3$ or $X_4$ is other than hydrogen and preferably that $X_1$ is hydroxy, Cl, F, Br, I, $CO_2H$, $NO_2$, $SO_3H$, $SO_2Cl$, SH, $NH_2$, NHR, $NR_2$, $CONR_2$, COR wherein R is $C_1$–$C_4$ alkyl or hydrogen and mixtures thereof; or the N-oxide thereof; or an acid addition salt therof; in aqeuous base with hydrogen peroxide.

Surprisingly, it has been found that formula II quinolines and preferably 8-substituted-quinolines are readily oxidized to pyridine-2,3-dicarboxylic acids with hydrogen peroxide in the presence of aqueous base, conditions where hydrogen peroxide is normally considered to be unstable.

DETAILED DESCRIPTION OF THE INVENTION

Aqueous bases suitable for use in the method of this invention include alkali metal and alkaline earth metal hydroxides and carbonates such as sodium, potassium, lithium and calcium hydroxides or carbonates and mixtures thereof, with aqueous sodium hydroxide and potassium hydroxide being preferred. In general, base concentrations of 15% to 35% on a weight basis are preferred for maximizing rates and reaction producivity. The use of higher concentrations is preferable depending upon the solubility of the starting quinoline but is not required.

The oxidation has been found to proceed with as little as one molar equivalent of aqueous base per mole of starting formula II quinoline with preferred stoichiometry of from four to seven molar equivalents of base giving optimum yields and purities, greater amounts can of course also be employed.

A minimum of eight molar equivalents of hydrogen peroxide is required to completely oxidize a Formula II quinoline by the method of this invention, typically 8 to 20 molar equivalents and preferably 9 to 14 molar equivalents of 30% to 50% aqueous hydrogen peroxide was added to a solution of the quinoline in the aqueous base at a rate which allows the temperature to be maintained in the preferred temperature range. Reaction with less than eight molar equivalents of hydrogen peroxide proceeds but gives reduced yields.

Temperature of the reaction has shown modest effect on the yield of the reaction. In general, the preferred temperature range is between 75° to 90° C. A practical upper limit is reflux (102° C. to 105° C.), higher temperatures can of course be achieved in a closed pressurized system but care must be exercised due to the possibility of liberating a large volume of oxygen from the decomposition of hydrogen peroxide. At lower temperatures excess hydrogen peroxide may be built up in the reaction due to a slower rate of reaction which may present a hang fire situation. At lower temperatures (50° C.), a solid liquid mixture may be formed depending on the concentration of the base. When solubility of the starting material in the aqueous base is a problem, water miscible co-solvents which are inert to the reaction conditions such as tert-butanol may be utilized in the reaction to aid in solubilizing the starting substituted quionoline in the reaction mixture. However, care must be taken to carefully evaluate the use of co-solvents for a particular reaction.

The yield of these reactions has been shown to be greatly influenced by some metals and metal ions. Metal ions such as chromium and nickel has little or no effect, but addition of small amounts of ferric chloride (~10 ppm) to reaction mixture lowers yields. The contact of the reaction solution with metals such as 304 or 316 stainless steel and Hastelloy C has also caused lower yields, while contact with metals such as nickel and zirconium and alloys such as Inconel has little or no effect on the yield.

Formula II starting 8-substituted-quinolines may readily be prepared by procedures known in the art such as the Skraup reaction, Doebner-Miller reaction or the sulfonation of quinoline.

In accordance with the preferred method of this invention 5-ethyl-pyridine-2,3-dicarboxylic acid may be prepared by adding 8 to 20 molar equivalents of 30% to 50% aqueous hydrogen peroxide over a 0.5 to 5 hour period to a solution of 3-ethyl-8-hydroxyquinoline in 4 to 7 molar equivalents of about 15% to 35% on a weight basis of aqueous sodium or potassium hydroxide in a temperature range of 75° to 90° C.

Upon completion of the peroxide addition, the reaction mixture is allowed to stir at the reaction temperature until complete (usually one to two hours), and the mixture is then tested for the presence of peroxides.

If peroxides are present potassium, ammonium or sodium bisulfite is added to destroy residual peroxide.

The product dicarboxylic acid may then be isolated by the acidification of the reaction mixture with a mineral acid and collected by standard procedures such as filtration or extraction into an organic solvent.

Alternatively, the method of this invention may be conducted in a continuous fashion by concurrently adding in separate streams the hydrogen peroxide, a portion of the aqueous base and a solution of the formula II quinoline, in a minimum amount of the aqueous base or aqueous acid required to obtain a solution, at the desired reaction temperature.

The reaction is further illustrated by the following non-limiting examples.

EXAMPLE 1

Preparation of 5-ethyl-pyridine-2,3-dicarboxylic acid with potassium hydroxide and hydrogen peroxide To a stirred mixture of 25% potassium hydroxide (215.5 g, 0.96 mol) and 3-ethyl-8-hydroxyquinoline (30.28 g, 0.175 mol) at 90° C. is added 277.5 g of 30% hydrogen peroxide (2.45 mol) over 3.25 hours maintaining the temperature at 90° C. for an additional one to two hours at which time the solution is tested for peroxides and if present destroyed with potassium bisulfite. The reaction is then distilled to remove 243 g of water to bring the reaction mixture to one half its original weight. The solution is cooled to 450° C. and sulfuric acid is added until a pH of 3.5 is obtained. The resulting slurry of potassium sulfate is cooled to 10° C., held for 30 minutes, filtered and washed with 5 mL of cold water. To the filtrate is added sulfuric acid until a pH of 1.8 is obtained. The resulting slurry of 5-ethyl-pyridine dicarboxylic acid is held at 10° C. for 30 minutes, filtered and washed with 20 mL of cold water. The filter cake is then dried at 55° C. under reduced pressure for three to eight hours to provide 19.60 g (97.6% purity) of the product as a light yellow to off white solid.

Utilizing the above procedure with various substituted quinolines, with differing quantities of a variety of aqueous bases of varying concentrations, with differing quantities of hydrogen peroxide of varying concentrations yields the pyridine-2,3-dicarboxylic acids under the reaction conditions listed in Table I below.

TABLE I

Preparation of pyridine 2,3-dicarboxylic acids

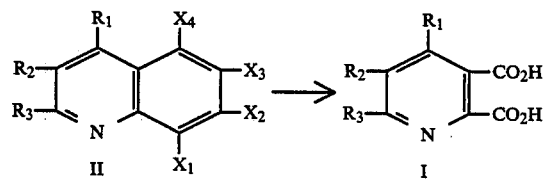

| Example | Formula II Compound R1 | R2 | R3 | X1 | X2 | X3 | X4 | mols | Base | Aqueous Base Conc. % w/w | mols | Aqueous H2O2 Conc. % w/w | mols | Temp °C. | Time hrs | Formula I Compound R1 | R2 | R3 | % Yield |
|---|---|---|---|---|---|---|---|---|---|---|---|---|---|---|---|---|---|---|---|
| 2 | H | C2H5 | H | OH | H | H | H | 1 | KOH | 31.7 | 6.6 | 50 | 20.0 | 90 | 3.25 | H | C2H5 | H | 61.0 |
| 3 | H | C2H5 | H | OH | H | H | H | 1 | KOH | 19.1 | 4.0 | 30 | 6.7 | 90 | 1.17 | H | C2H5 | H | 67.0 |
| 4 | H | C2H5 | H | OH | H | H | H | 1 | KOH | 17.3 | 4.0 | 30 | 10.0 | 90 | 1.5 | H | C2H5 | H | 70.5 |
| 5 | H | C2H5 | H | OH | H | H | H | 1 | KOH | 19.0 | 3.0 | 30 | 6.8 | 90 | 1.17 | H | C2H5 | H | 62.5 |
| 6 | H | C2H5 | H | OH | H | H | H | 1 | KOH | 25.0 | 5.4 | 30 | 14.3 | 90 | 3.25 | H | C2H5 | H | 80.0 |
| 7 | H | C2H5 | H | OH | H | H | H | 1 | KOH | 29.5 | 5.7 | 30 | 12.2 | 90 | 3.66 | H | C2H5 | H | 81.0 |
| 8 HCl Salt | H | C2H5 | H | OH | H | H | H | 1 | KOH | 33.0 | 6.8 | 30 | 12.5 | 90 | 3.5 | H | C2H5 | H | 77.0 |
| 9 | H | C2H5 | H | OH | H | H | H | 1 | NaOH | 15.2 | 5.6 | 30 | 14.0 | 70–80 | 1.75 | H | C2H5 | H | 73.0 |
| 10 | H | C2H5 | H | OH | H | H | H | 1 | NaOH | 18.0 | 5.6 | 30 | 10.0 | 90 | 1.33 | H | C2H5 | H | 75.5 |
| 11 | H | H | H | OH | H | H | H | 1 | KOH | 24.9 | 7.5 | 50 | 20.0 | 70–80 | 3.25 | H | H | H | 87.7 |

EXAMPLE 12

Preparation of 5-methyl-pyridinedicarboxylic acid with potassium hydroxide and hydrogen peroxide Hydrogen peroxide (30% w/w, 92.7 g, 0.818 mols) is added over a 1.5 hour period to a stirred mixture of 26.4% aqueous potassium hydroxide (145.6 g, 0.665 mols) and 3-methyl-8-hydroxyquinoline hydrochloride (20.00 g, 0.102 mols) at 75° C. to 800° C. maintaining the temperature at 75° C. to 80° C. The reaction solution is then held at 75° C. to 80° C. for two hours and then heated at 90° C. to 95° C. for one hour. The reaction mixture is cooled at 35° C., and hydrochloric acid is added until a pH of 1.8 to 1.6 is obtained. The resulting slurry is stirred one hour at 20° C., filtered, washed with 30 mL of water and air dried for 12 hours to provide 14.6 g (purity 96.1%) of the title product as an off white to light yellow solid.

EXAMPLE 13

Preparation of pyridine-2,3-dicarboxylic acid N-oxide with potassium hydroxide and hydrogen peroxide Hydrogen peroxide (30% w/w, 31.64 g, 279.1 mols) is added to a stirred mixture of 8-hydroxyquinoline-N-oxide (5.00 g, 31.06 mols) and 7.95% aqueous potassium hydroxide (43.99 g, 62.42 mols) at 90° C. maintaining the temperature at 90° C. After 5 mL of hydrogen peroxide is added the addition is stopped, 10 mL of water is added, and the pH adjusted to 11.6 and held for 35 minutes. The peroxide addition is then continued over 83 minutes maintaining the pH at 11.6 with 45% potassium hydroxide. After stirring the reaction mixture for one hour at 90° C. an assay of the solution indicates a 56% yield of pyridine-2,3-dicarboxylic acid-N-oxide.

EXAMPLE 14

Preparation of 3-ethyl-8-hydroxyquinoline

2-Ethylacrolein (161.5 g) is added over a two hour period to a stirred mixture of o-aminophenol (296 g, 1.0 mol) and o-nitrophenol in 37% aqeuous hydrochloric acid (296 g) at a temperature of 100° C. The reaction mixture is allowed to stir at 100° C. for two hours and is then cooled to room temperature. Methylene chloride is added to the cooled reaction mixture and the pH of the mixture is adjusted to pH 7.0 with concentrated ammonium hydroxide while stirring. The organic phase is removed and concentrated under reduced pressure. Vaccum distillation of the residue at 5 mm Hg collecting the distillate having a vapor temperature of 130° C. to 165° C. gives 3-ethyl-8-hydroxyquinoline of 93% to 98% purity as determined by assay using high performance liquid chromatograph.

Utilizing the above procedure and substituting 2-methylacrolein or acrolein for 2-ethylacrolein yields 3-methyl-8-hydroxyquinoline or 8-hydroxyquinoline respectively.

What is claimed is:

1. A method for the preparation of unsubstituted and substituted pyridine-2,3-dicarboxylic acids of formula I

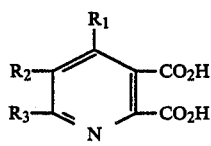

wherein $R_1$, $R_2$ and $R_3$ are each hydrogen, $C_1$-$C_6$ alkyl, hydroxy-$C_1$-$C_6$ alkyl, $C_1$-$C_6$ alkoxy, phenoxy, $C_1$-$C_4$ haloalkyl, nitro, hydroxy, amino, $C_1$-$C_4$ alkylamino, diloweralkylamino or $C_1$-$C_4$ alkylamino, diloweralkylamino or $C_1$-$C_4$ alkylsulfonyl group, carboxy, acyl, amido; or phenyl optionally substituted with one $C_1$-$C_1$ alkyl, $C_1$-$C_4$ alkoxy or halogen; difluoromethoxy, trifluoromethoxy, 1,1,2,2-tetrafluoroethoxy, $C_3$-$C_8$ straight or branched alkenyloxy optionally substituted with one to three halogens, or $C_3$-$C_8$ straight or branched alkynyloxy optionally substituted with one to three halogens; and when taken together, $R_2$ and $R_3$ may form a ring which may optionally be substituted, in which $R_2R_3$ are represented by —$(CH_2)_2$—Q— or —$(CH_2)_2$—Q—, wherein Q is oxygen, sulfur, or nitrogen, with the proviso that $R_1$ is hydrogen; comprising oxidizing a substituted quinoline of formula II

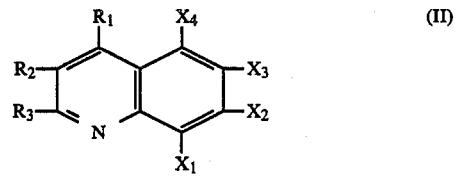

wherein $R_1$, $R_3$ and $R_3$ are as described in formula I above; $X_1$, $X_2$, $X_3$, $X_4$ are each hydroxy, hydrogen, $SO_3H$, $SO_2Cl$, SH, Cl, F, Br, I, $CO_2H$, $NO_2$, or $NR_2$, $CONR_2$ or COR wherein R is $C_1$-$C_4$ alkyl or hydrogen; with the proviso that one of $X_1$, $X_2$, $X_3$ or $X_4$ is other than hydrogen; or the N-oxide thereof; or an acid addition salt thereof; in aqueous base with hydrogen peroxide.

2. A method according to claim 1 wherein about eight to twenty molar equivalents of hydrogen peroxide are added to a stirred solution of a formula II quinoline in a minimum of one molar equivalent of aqueous base; in a temperature range of about 75° C. to 90° C.

3. A method according to claim 2 wherein the quinoline is dissolved in four to seven molar equivalents of aqueous base of a concentration of about 15% to 35% on a weight basis.

4. A method according to claim 3 wherein the base is potassium hydroxide or sodium hydroxide.

5. A method according to claim 4 for the preparation of 4-substituted, 5-substituted, 6-substituted, 4,5-disubstituted, 4,6-disubstituted and 5,6-disubstituted alkyl-pyridine-2,3-dicarboxylic acids, the N-oxides thereof; wherein $X_1$ is hydroxy, Cl, F, Br, I, $CO_2H$, $NO_2$, $SO_3H$, $SO_2Cl$, SH, $NR_2$, $CONR_2$, COR wherein R is $C_1$-$C_4$ alkyl or hydrogen.

6. A method according to claim 5 for the preparation of 5-ethyl-pyridine-2,3-dicarboxylic acid from 3-ethyl-8-hydroxyquinoline or an acid addition salt thereof.

7. A method according to claim 5 for the preparation of 5-methyl-pyridine-2,3-dicarboxylic acid from 3-methyl-8-hydroxyquinoline or an acid addition salt thereof.

8. A method according to claim 4 for the preparation of pyridine-2,3-dicarboxylic acid from 8-hydroxyquinoline or an acid addition salt thereof.

9. A method according to claim 5 for the preparation of 5-ethyl-pyridine-2,3-dicarboxylic acid N-oxide from 3-ethyl-8-hydroxyquinoline-N-oxide or an acid addition salt thereof.

10. A method according to claim 5 for the preparation of 5-methyl-pyridine-2,3-dicarboxylic acid N-oxide from 3-methyl-8-hydroxyquinoline-N-oxide or an acid addition salt thereof.

11. A method according to claim 4 for the preparation of pyridine-2,3-dicarboxylic acid N-oxide from 8-hydroxyquinoline N-oxide or an acid addition salt thereof.

* * * * *

UNITED STATES PATENT OFFICE
CERTIFICATE OF CORRECTION

Patent No. 4,816,588　　　　　Dated March 28, 1989

Inventor(s)　Rieker et al.

It is certified that error appears in the above-identified patent and that said Letters Patent is hereby corrected as shown below:

Col. 8, line 20, "$R_3$", first occurrence, should read -- $R_2$ --.

Col. 8, line 20, after "described", "in" should read -- for --.

Col. 8, line 22, after "$NO_2$,", "or" should be deleted and -- $NH_2$; or NHR -- should be inserted.

Signed and Sealed this

Seventeenth Day of October, 1989

Attest:

DONALD J. QUIGG

Attesting Officer　　　Commissioner of Patents and Trademarks

Disclaimer 4,816,588.—*William F. Rieker,* Plainsboro; *William A. Daniels,* Belle Mead, both of N.J. METHOD FOR THE PREPARATION OF PYRIDINE-2, 3-DICARBOXYLIC ACIDS. Patent dated Mar. 28, 1989, Disclaimer filed Oct. 12, 1989, by the assignee, American Cyanamid Company.

The term of this patent subsequent to October 10, 1989, has been disclaimed.
*[Official Gazette September 18, 1990 ]*